United States Patent
Marcus (10) Patent No.: US 11,484,257 B2
(45) Date of Patent: Nov. 1, 2022

(54) MUSCLE AND FASCIA PAIN IDENTIFICATION BY ELECTRICAL STIMULUS

(71) Applicant: Norman J. Marcus, New York, NY (US)

(72) Inventor: Norman J. Marcus, New York, NY (US)

(*) Notice: Subject to any disclaimer, the term of this patent is extended or adjusted under 35 U.S.C. 154(b) by 0 days.

(21) Appl. No.: 17/650,802

(22) Filed: Feb. 11, 2022

(65) Prior Publication Data

US 2022/0257179 A1    Aug. 18, 2022

Related U.S. Application Data (60) Provisional application No. 63/148,911, filed on Feb. 12, 2021.

(51) Int. Cl.
  *A61B 5/00*    (2006.01)

(52) U.S. Cl.
  CPC .......... *A61B 5/4824* (2013.01); *A61B 5/4519* (2013.01); *A61B 5/748* (2013.01); *A61B 5/7435* (2013.01)

(58) Field of Classification Search
  CPC ... A61B 5/4824; A61B 5/4519; A61B 5/7435; A61B 5/748; A61B 5/08; A61N 1/328; A61N 1/36021
  See application file for complete search history.

(56) References Cited

U.S. PATENT DOCUMENTS

| | | | | |
|---|---|---|---|---|
| 6,058,938 A | * | 5/2000 | Chu | A61N 1/36021 128/898 |
| 2006/0224210 A1 | * | 10/2006 | Stellar | A61B 5/4519 607/46 |
| 2013/0204097 A1 | * | 8/2013 | Rondoni | A61B 5/08 600/453 |
| 2016/0310730 A1 | | 10/2016 | Martins et al. | |
| 2018/0125689 A1 | | 5/2018 | Perez et al. | |
| 2019/0336073 A1 | | 11/2019 | Kirkup et al. | |

FOREIGN PATENT DOCUMENTS

WO    WO2015160964    10/2015

OTHER PUBLICATIONS

International Search Report and Written Opinion in International Appln. No. PCT/US2022/016187, dated Jun. 22, 2022, 11 pages.

* cited by examiner

*Primary Examiner* — Patrick Fernandes
(74) *Attorney, Agent, or Firm* — Fish & Richardson P.C.

(57) ABSTRACT

A nerve stimulation system including a stimulation probe including a handle and a stimulation head at an end of the handle; a reference electrode; and a control system in communication with the stimulation probe and the reference electrode, the control system configured to generate an electrical stimulation signal that, when delivered to a skin surface of a patient using the stimulation probe, induces an activation potential in a plurality of nociceptors while remaining below a threshold that induces a muscle contractile response.

9 Claims, 10 Drawing Sheets

| | A | B | C | D | E | F |
|---|---|---|---|---|---|---|
| 1 | John Doe | | | | | |
| 2 | MUSCLE | SIDE | RESPONSE | DATE TESTED | TREATED | DATE TREATED |
| 3 | Sternohyoid | Right | Persistent | 5/9/2019 | | |
| 4 | Sternocleidomastoid | Right | No Response | | | |
| 5 | Splenius Capitis | Right | Transient | 5/9/2019 | | |
| 6 | Spinalis Cervicis | Right | Persistent | 5/9/2019 | | |
| 7 | Spinalis Cervicis | Right | Persistent | 5/9/2019 | | |
| 8 | Splenius Capitis | Right | Transient | 5/9/2019 | | |
| 9 | Sternocleidomastoid | Right | No Response | 5/9/2019 | | |
| 10 | Pectoralis Minor | Right | No Response | 5/9/2019 | | |
| 11 | Pectoralis Major | Right | Transient | 5/9/2019 | | |
| 12 | Internal Intercostals | Right | Transient | 5/9/2019 | | |
| 13 | Innermost Intercostals | Right | Transient | 5/9/2019 | | |
| 14 | Diaphram | Right | No Response | 5/9/2019 | | |
| 15 | Deltoid | Right | Persistent | 5/9/2019 | | |
| 16 | Rectus Abdominis | Right | Persistent | 5/9/2019 | | |
| 17 | Internal Oblique | Right | Persistent | 5/9/2019 | | |
| 18 | Transverse Abdominis | Right | No Response | 5/9/2019 | | |
| 19 | | | | | | |
| 20 | | | | | | |
| 21 | | | | | | |

FIG. 8

Patient Info
Date:

Patient Name:
Patient Age:
Diagnosis:

Chief Complaint:

History of Onset and Pertinent Treatment:

MUSCLE AND FASCIA PAIN IDENTIFICATION BY ELECTRICAL STIMULUS

CLAIM OF PRIORITY

This application claims priority under 35 USC § 119(e) to U.S. Patent Application Ser. No. 63/148,911, filed on Feb. 12, 2021, the entire contents of which are hereby incorporated by reference.

FIELD OF THE DISCLOSURE

This disclosure relates to the use of low magnitude electrical stimulus to identify sensitized nociceptors.

BACKGROUND

The most common diagnosis of low back and neck pain is "nonspecific pain" defined as sprains and strains of soft tissue. Pain emanating from muscle is a result of stimulation of nociceptors in the specific pain generating muscle(s). Muscle nociceptors are high threshold mechanoreceptors (and chemoreceptors) that under normal conditions will only respond to potential or actual tissue damaging stimuli. Various degrees of trauma can alter the nociceptor producing a reduction in the threshold to depolarize the nociceptor (referred to as sensitization), thus creating a state in which normal use of the muscle may cause persistent pain. Currently, there is no instrument that assesses the presence of sensitized nociceptors in pain-producing tissue in a suspected muscle or muscle group.

The community standard to assess pain-causing muscles generally addresses tender areas in muscle tissue called trigger points (TrPs). Trigger points are defined as areas of muscle tenderness, identified by palpation (pressure applied to muscle tissue), that often radiate pain to adjacent areas. The community standard of care for these TrPs focuses on treatment with a variety of needling or massage techniques.

Identification of an entire specific muscle, as opposed to identification of TrPs which may not result in the identification of a specific muscle (e.g., diagnosing TrPs in cervical, thoracic, or lumbar paraspinal tissue or in Erector Spinae Musculature), as the source of persistent pain leads to more effective treatment. The nociceptors in a muscle producing pain are most densely populated at the ends of the muscle (e.g., the attachment sites/the origin and insertion). Identification of an entire specific muscle allows for the location of the attachment sites.

SUMMARY

This disclosure describes systems and methods for identifying sensitized muscles (SM) defined as muscles whose nociceptors are sensitized (e.g., have a lower threshold to be depolarized) using low magnitude electrical stimuli. For example, disclosed herein is a diagnostic system which transmits an electrical stimulation signal into targeted muscles inducing a pressure sensation in the entirety of a SM while not causing any subjective response in non-sensitized muscle.

In a first aspect, this disclosure is directed to a nerve stimulation system including a stimulation probe including a handle and a stimulation head at an end of the handle; a reference electrode: and a control system in communication with the stimulation probe and the reference electrode, the control system configured to generate an electrical stimulation signal that, when delivered to a skin surface of a patient using the stimulation probe, induces an activation potential in a plurality of nociceptors while remaining below a threshold that induces a muscle contractile response.

In some embodiments, the handle of the stimulation probe can include a modulation button and at least one control button. The stimulation head of the stimulation probe can include a conductive material. The conductive material can be aluminum, stainless steel, tungsten, or titanium. The sensor head of the stimulation probe can include a flat surface.

The stimulation signal can include a carrier wave and a modulation wave. The carrier wave and modulation wave can have a respective frequency parameter and a respective amplitude parameter. The carrier wave frequency parameter can be between 0.1 kHz and 10 kHz. The modulation wave frequency parameter can be between 0.01 kHz and 1 kHz. The stimulation signal can be voltage controlled in a range from 0.1 to 10 Volts. The stimulation signal can be current controlled in a range from 0.5 to 4 milliamperes.

In a second aspect, this disclosure is directed to a sensitized muscle identification method including selecting a first muscle to be tested; placing a sensor head of an electrical stimulation probe in contact with a first skin surface of a patient, the first skin surface being proximate to the first muscle; and applying a stimulation signal to the first skin surface along the entire course of the muscle from origin to insertion using the sensor head to induce an activation potential in a plurality of sensitized nociceptors present in the first muscle while remaining below a threshold that induces a muscle contractile response in the first muscle, wherein the activation potential in the plurality of sensitized nociceptors induces a pressure sensation in the first muscle that is experienced by the patient.

In some embodiments, the method can further include recording a patient response corresponding to the pressure sensation experienced by the patient. The method can further include determining a treatment method for the first muscle based upon the pressure sensation in the first muscle that can be experienced by the patient and the presence of the plurality of sensitized nociceptors.

In some embodiments, the method can further include selecting a second muscle to be tested; placing a sensor head of an electrical stimulation probe in contact with a second skin surface of a patient, the second skin surface being proximate to the second muscle; and applying a stimulation signal to the second skin surface along the entire course of the muscle from origin to insertion using the sensor head to induce an activation potential in a plurality of sensitized nociceptors present in the selected second muscle while remaining below a threshold that induces muscle contractile response, wherein the activation potential in the plurality of sensitized nociceptors induces a pressure sensation in the second muscle that can be experienced by the patient.

In some embodiments, the method can further include, between selecting the first muscle and placing the sensor head, applying a conductive material to the first skin surface proximate to the first muscle. The conductive material can be a gel, liquid, paste, or powder.

The systems and processes described here may be used to provide one or more of the following optional benefits. First, chronic pain generating muscles and the enshrouding fascia including sensitized nociceptors can be identified with a high degree of accuracy. This can simplify and increase the efficacy of subsequent treatment methods. The stimulation signal delivered by the systems described herein includes components that trigger an action potential in sensitized nociceptors while not triggering an action potential in non-sensitized nociceptors.

Additionally, as nociceptors are more densely located in the origin and insertion points of a muscle, identification of specific sensitized muscle and/or fascia facilitates identification of those specific muscles' attachment sites which contain the density of that muscle's nociceptors and therefore of desired targets for future treatment. User operation of the device in conjunction with accurate visual depictions of the human musculoskeletal system facilitates specific identification of individual muscles within a muscular group.

Second, the minimal stimulation signal delivered to a patient's skin surface produces a current that is advantageously beneath the threshold which would elicit a contractile response in the muscle (e.g., twitching) or stimulate sensory fibers in the skin to produce any sensation. A contractile response and/or a sensation in the skin may mask the sensation produced solely by a sensitized nociceptor. Delivering a stimulation signal that will not stimulate muscle contraction or cutaneous sensation is fundamental to the effectiveness of the instrument.

BRIEF DESCRIPTION OF THE DRAWINGS

In the figures, like symbols indicate like elements.

DETAILED DESCRIPTION

Systems, devices, and methods for identifying a sensitized muscle through stimulation of sensitized nociceptors in muscle and fascia are described in this disclosure.

A stimulus to a muscle of sufficient magnitude induces a threshold potential within a neuron wherein the neuron becomes depolarized, transmitting a signal to nearby neurons. This traveling signal is known as an action potential. High threshold potential sensory neurons, termed nociceptors, generate action potentials related to strong stimuli, capable of causing, or potentially causing, tissue damage. The trauma producing such stimuli causes the nociceptors to transmit information processed by the brain as pain.

When a muscle has been misused, overloaded, or repeatedly minimally injured, the threshold to depolarize a nociceptor may be lowered, causing trivial stimuli to be perceived as painful. As used herein, the state of lowered threshold potential is called "sensitization." A lowered threshold potential includes a lowered activation threshold to produce an action potential. Sensitized muscle nociceptors are a source of pain in patients with chronic regional pain such as low back pain, neck pain and shoulder pain as common but not exclusive examples.

Strong stimuli are needed to excite nociceptors, but a sensitized nociceptor will be stimulated with minimal provocation. Accordingly, movement or use of the muscle for normal tasks (e.g., lifting a relatively light object) elicits an action potential in a sensitized nociceptor. Sensitized nociceptors are present throughout an entire pain-presenting muscle suggesting that the fascia overlying the muscle also contains sensitized nociceptors and can be targeted for therapeutics. In particular, the origin and insertion points of a muscle contain the highest concentration of nociceptors making the identification of a specific muscle, thus enabling the identification of its attachment points, a crucial element in the diagnosis of the pain source since knowledge of the specific muscle will direct the clinician to the muscle attachment sites to maximize the effect of any treatment rendered to a specific muscle.

Figure 1:
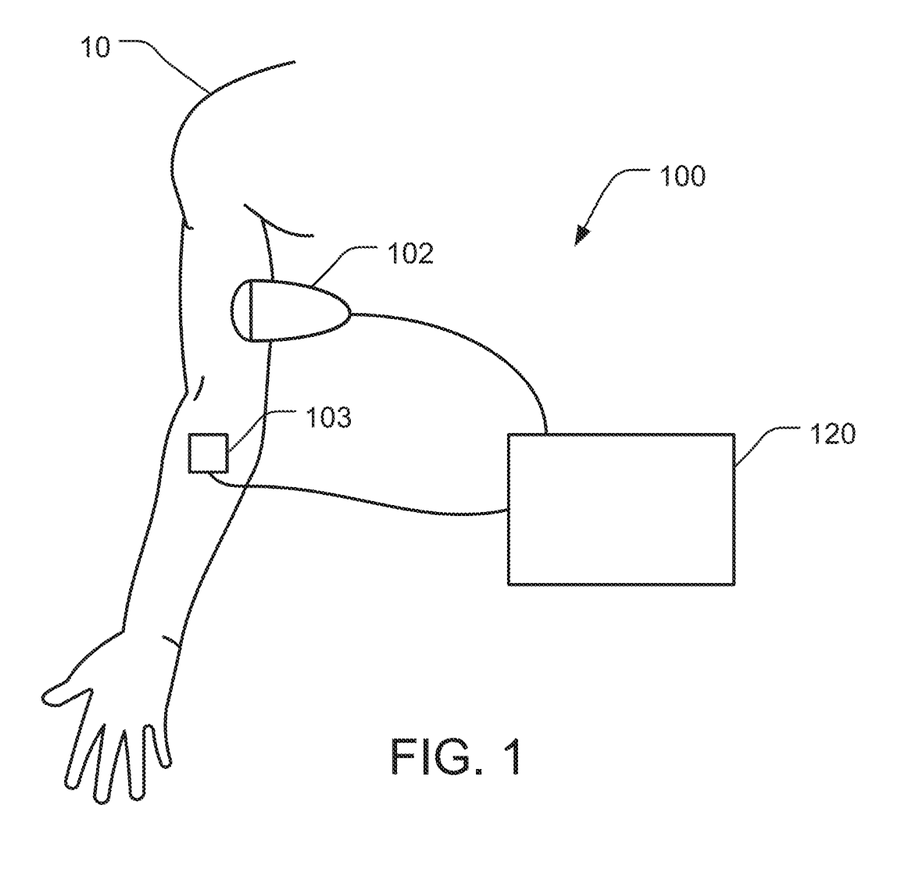
FIG. 1 is a schematic diagram of an example nociceptor stimulating system in contact with a patient.

FIG. 1 depicts a nociceptor stimulation system 100. The nociceptor stimulation system 100 can be used for identifying sensitized nociceptors within muscles and/or muscular fascia as described further below. The nociceptor stimulation system 100 is alternatively termed a sensitized muscle identification system 100.

The stimulation system 100 includes a non-invasive electrical stimulation probe 102 and a reference electrode 103 in contact with a skin contact surface of a patient 10 (e.g., the arm). The non-invasive stimulation probe 102 and reference electrode 103 are also in wired electronic communication with a control system 120 of the stimulation system 100.

To identify sensitized nociceptors, e.g., muscles containing sensitized nociceptors, e.g., sensitized muscles, the reference electrode 103 is placed in contact with the skin of a patient 10, providing a ground for an electrical stimulation signal delivered by the stimulation probe 102. In operation, the control system 120 generates and transmits a stimulation signal to the stimulation probe 102. The stimulation probe surface contacting the skin of the patient 10 is a conductive sensor head which transmits the stimulation signal through the skin to the muscle and fascia beneath the stimulation probe 102.

The amplitude of the stimulation signal is greater than the action potential threshold of sensitized nociceptors (but not non-sensitized nociceptors) present in a muscle and enshrouding fascia of the muscle, thereby generating an action potential in sensitized nociceptors. The generated action potential is physically experienced by the patient 10 as a pressure sensation which is recorded by the clinician user (or simply "user" hereinafter). A pressure sensation response can include a reported degree of pressure sensation experienced by the user. For example, a pressure sensation can be experienced along the entirety of the identified muscle, e.g., from muscle origin to insertion. A pressure sensation can be experienced along only a portion of the suspected muscle, which can indicate that an adjacent or antagonist muscle is a source of pain.

In some implementations, the pressure sensation is reported by the patient 10 as a sensation of discomfort, e.g., a discomfort sensation. The sensation of discomfort can include, but is not limited to, sensations of pressure, tenderness, or soreness. In some implementations, the sensation of discomfort is identified by the patient 10 as a lack of pressure sensation after the identification signal is terminated. The sensation of discomfort can be experienced along the entirety of the identified muscle, e.g., from muscle origin to insertion. A partial sensation of discomfort can be experienced along a portion of the identified muscle. A partial sensation of discomfort can indicate an adjacent or antagonist muscle is a source of pain.

In some implementations, the patient 10 is the user and the pressure sensation experienced by the patient 10 is recorded by the patient 10, e.g., self-recording of results. For example, the patient 10 can self-record results outside of a clinical setting. The patient 10 can communicate, e.g., electronically communicate, the self-recorded results to a clinician user. For example, the patient 10 can communicate the self-recorded result to the clinician user over a telephonic network, or an electronic network, e.g., the internet.

The stimulation signal amplitude delivered by the stimulation probe 102 is lower than the action potential threshold of non-sensitized nociceptors. Said another way, the stimulation signal delivered by the stimulation probe 102 is not stimulating an action potential in non-sensitized nociceptors, which exist as high threshold mechanoreceptors.

The electronic communication between the stimulation probe 102 and control system 120 is depicted as a wire, though in general can be wired or wireless (e.g., Wi-Fi, Bluetooth™, etc.).

Figure 2:
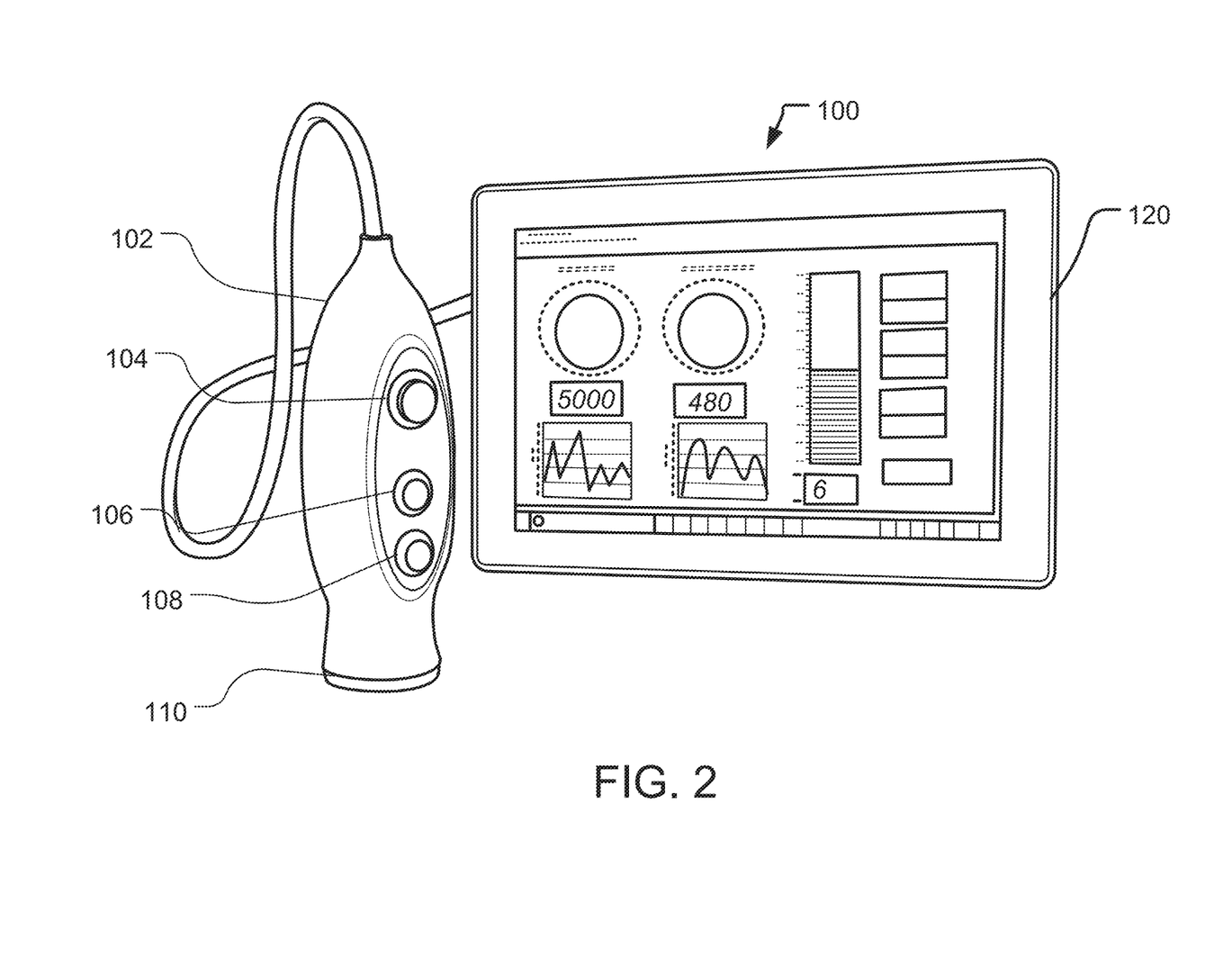
FIG. 2 is an image further depicting the nociceptor stimulating system of FIG. 1.

FIG. 2 is an image depicting an example stimulation probe 102 and an example control system 120 of the nociceptor stimulation system 100. The stimulation probe 102 housing is rigid and ergonomically shaped to be held and operated in one hand by a user. The stimulation probe 102 includes at least one operable control device (e.g., buttons, dials, or switches) that allow the user to control with a single hand one or more aspects of the nociceptor stimulation system 100. The controls can be for adjusting parameters such as, but not limited to, stimulation signal parameters, to record patient 10 response data, to enter stimulation sensation presence or magnitude, and the like.

The controls of the stimulation probe 102 shown in FIG. 2 include a stimulation signal modulation button 104, and control buttons 106 and 108. The modulation button 104 is depressed to modulate the presence or absence of the stimulation signal (e.g., stimulation signal on or off) at the stimulation head 110.

The control buttons 106 and 108 are operated by the user to perform context-dependent operations. For example, the control buttons 106 and 108 can be operated by the user to record the presence, duration, or absence of the pressure sensation experienced by the patient 10. As a further example, the control buttons 106 and 108 can be operated to increase or reduce one or more signal parameters of the stimulation signal. In a third example, the control buttons 106 and 108 can be operated to sequentially select one or more muscles to be targeted by the probe 102 as displayed by the control system 120.

The stimulation head 110 is composed of conductive material (e.g., aluminum, stainless steel, tungsten, or titanium) such that when placed in contact with a skin surface (e.g., the skin) of the patient 10 proximate to the muscle to be identified, the sensor head 110 creates a conductive electrical connection with the patient 10 skin and the stimulation signal is transmitted to the muscle and fascia. In some implementations, conductive gel can be applied to the skin of the patient 10 (or to the sensor head 110) to increase the conductance of the contact area before identification of sensitized nociceptors.

The stimulation head 110 circumference depicted in FIG. 2 is circular with a flat contact surface. In general, the sensor head 110 circumference shape can be other geometric shapes (e.g., rectangular) and the contact surface can be at least partially convex (e.g., hemispherical, or rounded) or concave.

Figure 3:
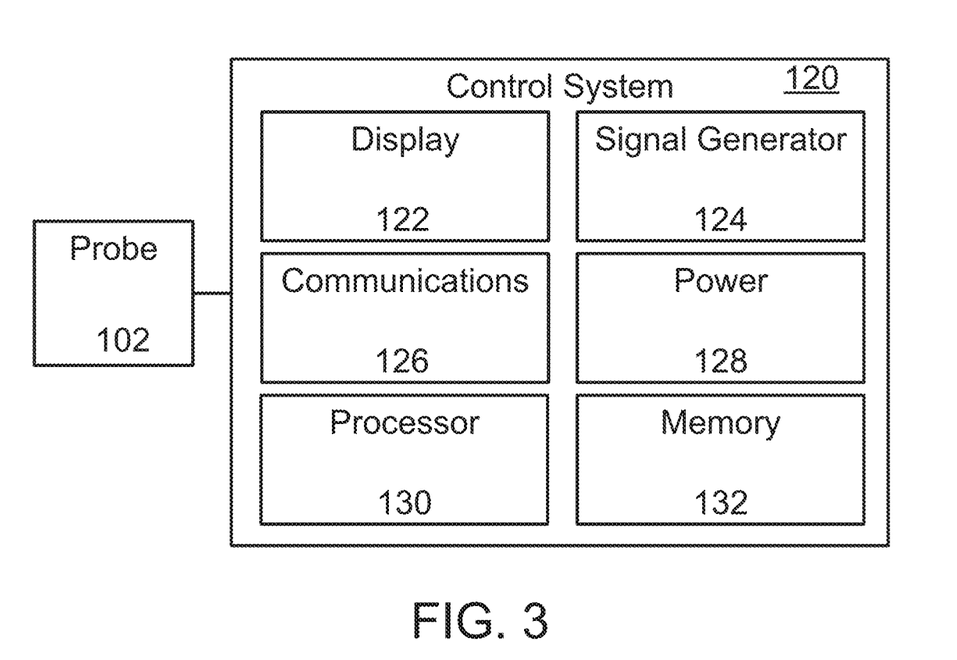
FIG. 3 is a schematic chart of the electrical components of the nociceptor stimulating device.

Referring now to FIG. 3, further details of the example control system 120 are schematically shown. The control system 120 includes a display 122, signal generator 124, communications unit 126, power supply 128, processor 130, and memory 132. The display 122 is a monitor device capable of displaying information such as the stimulation signal characteristics to the user. The display 122 can be integrated into the housing of the control system 120 or connected externally through a data (e.g., USB), video (e.g., DVI), or combined data/video connection (e.g., HDMI) to the communications unit 126. In some embodiments, the display 122 is a touchscreen device (e.g., tablet) or a computing unit capable of user interaction and data input and processing (e.g., a laptop, smart phone, or personal computer).

The communications unit 126 may provide communication with the processor 130 and other connected internal or external units of the control system 120. The communications unit 126 may provide, for example, wired communication with the probe 102 or wireless communication with external devices. The control system 120 may communicate wirelessly through the communications unit 126, which may include digital signal generation circuitry where necessary, such as using a Bluetooth, Wi-Fi, or other such transceiver.

The power supply 128 supplies electrical power to the other elements of the control system 120 and to attached peripherals (e.g., probe 102) of the control system 120 using external (e.g., outlet) or internal (e.g., batteries) power sources.

The processor 130 executes instructions within the control system 120, including instructions stored in the memory 132. The processor 130 may be implemented as a chipset of chips that include separate and multiple analog and digital processors. The processor 130 may provide, for example, for coordination of the other components of the control system 120, such as control of user interfaces, or applications run by the control system 120.

The processor 130 may communicate with a user through a control interface displayed on the display 122. The display 122 may be, for example, a TFT (Thin-Film-Transistor Liquid Crystal Display) display or an OLED (Organic Light Emitting Diode) display to present graphical and other information to a user. The control interface may receive commands from a user and convert them for submission to the processor 130. Alternatively, or in addition, the processor 130 may communicate with a user through additional user interface methods such as a keyboard, mouse, trackball, number pad, or networked application.

The memory 132 stores information within the control system 120. The memory 132 can be implemented as one or more computer-readable medium, such as a volatile or non-volatile memory unit (e.g., flash memory and/or NVRAM memory). When executed by processor 130, the instructions stored in the memory 132 perform one or more functions such as any identification method as described herein.

The information stored in the memory 132 can include patient identification information which can be considered protected health information according to one or more standards of patient care (e.g., HIPAA). The information stored in memory 132 including identifying patient information can be stored in an encrypted form according to an encryption standard that meets or exceeds the standard of patient care. For example, the information stored in memory can be encrypted using Advanced Encryption Standard (AES) 128, 192, or 256-bit encryption, Open PGP, or S/MIME encryption.

The signal generator 124 produces the stimulation signal(s) which is/are transmitted to the probe 102. The signal generation unit 124 includes circuitry components necessary to generate the stimulation signal according to parameters input by the user or stored in the memory 132. The circuitry components can include additional processors (such as processor 130), amplifiers, integrated circuits (e.g., field programmable gate arrays, or application specific integrated circuits), analog-to-digital converters, or transformers.

The signal generator unit 124 generates types of stimulation signals. In some embodiments, the stimulation signals are composed of a carrier wave multiplied by a modulation wave. The carrier wave and modulation waves can be sine waves, square waves, sawtooth waves, or rectangular waves, and the product of the carrier wave and modulation waves is a superposition of both. The carrier wave and modulation waves have two respective parameters, a frequency and an amplitude. These parameters are stored in memory 132 and supplied to the signal generator 124 to generate and multiply the carrier wave and modulation waves into the stimulation signal supplied to the probe 102. The frequency of the carrier and modulation waves can be modified by the control system 120 automatically and/or modified by the user through the display. The stimulation signal can be current, or voltage controlled.

In general, the carrier wave includes a higher frequency parameter than the modulation wave such that the higher-frequency carrier wave transmits the lower-frequency modulation wave through the skin of a patient and the modulation wave induces stimulation in the underlying nerves in muscle and fascia. For example, a stimulation signal can be produced using a sinusoidal carrier wave at a frequency of 5 kHz multiplied by a sinusoidal modulation wave at a frequency of 0.5 kHz. Carrier wave frequencies can be between 0.1 kHz and 10 kHz and modulation wave frequencies can be between 0.1 kHz and 1 kHz. The amplitude parameters of the carrier and modulation waves are measured in peak-to-peak voltage (Vpp) and can be between 0.1 and 10 Vpp. In some embodiments, the carrier and modulation wave amplitude parameters can be controlled by the control system 120. In the current control mode, the carrier and modulation wave current parameters (e.g., current amplitude) can be controlled by the control system 120 in a range between 0.5 and 4 milliamps peak.

Figure 4:
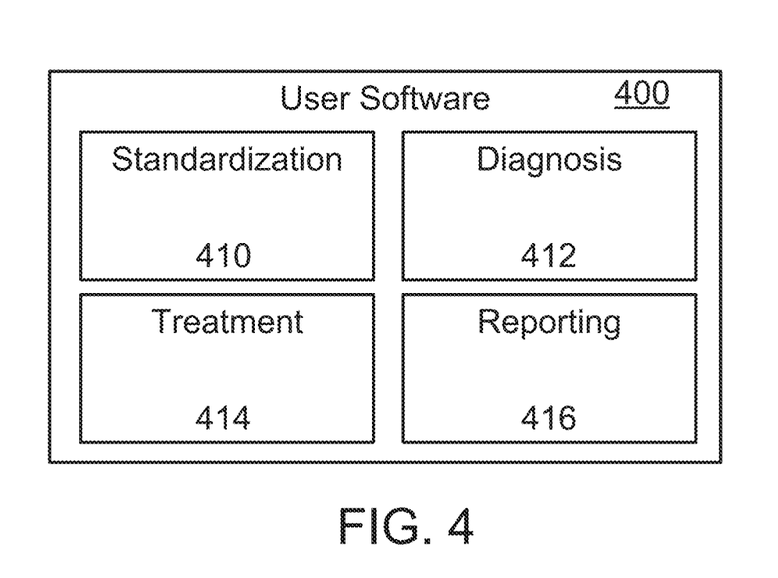
FIG. 4 is a schematic chart of the components of the user software of the nociceptor stimulating device.

FIG. 4 depicts details of the modules of user interface software 400 schematically. The user interface software 400 includes a standardization module 410, a diagnosis module 412, a treatment module 414, and a reporting module 416. In some embodiments, the user interface software 400 can include additional modules for alternative user interface components. The code for executing the user interface software 400 and modules 410, 412, 414, and 416 can be stored in the memory 132 of the control system 120 and executed on processor 130.

Figure 5:
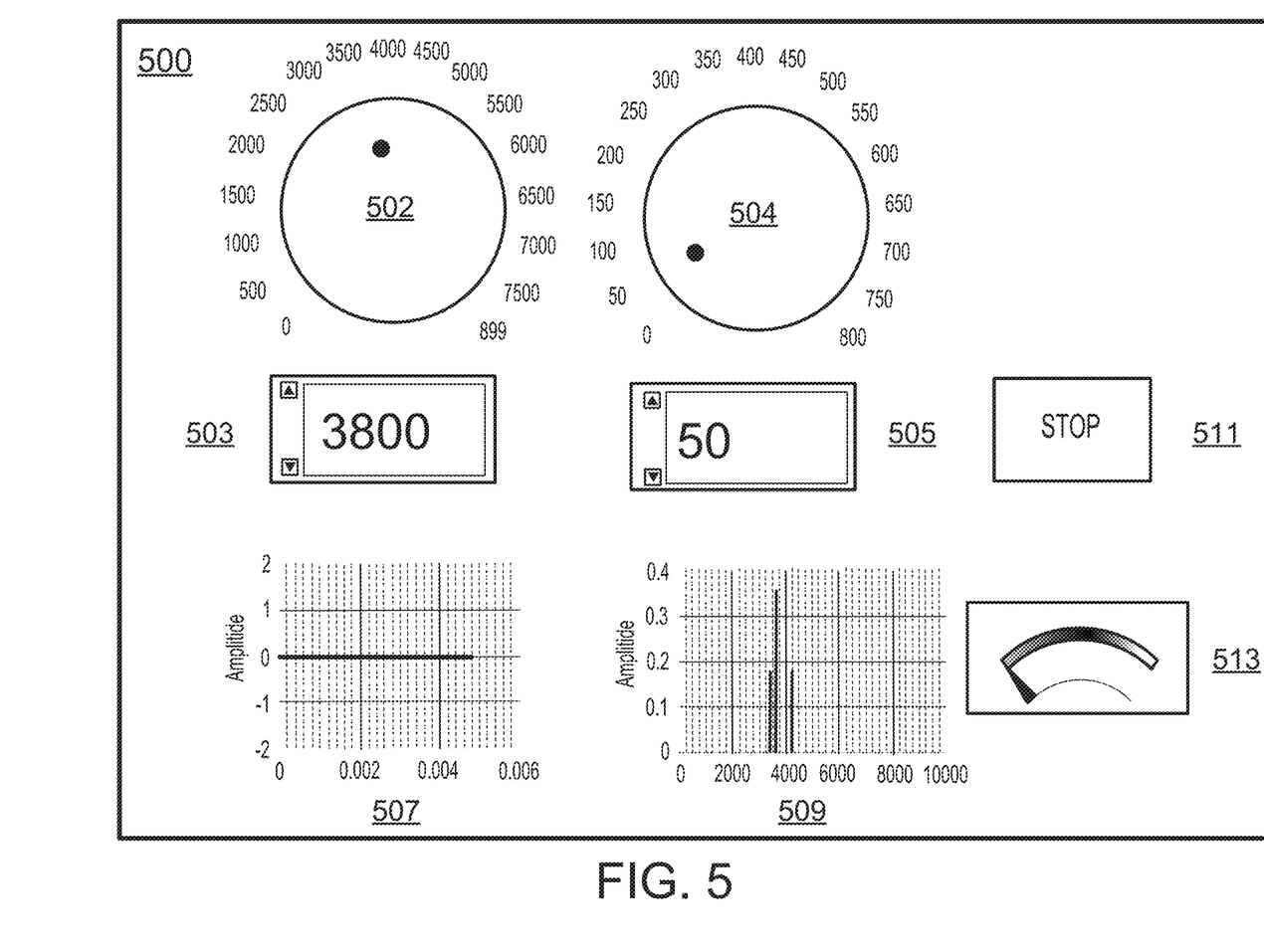
FIG. 5 is an image depicting an exemplary user interface control screen of the standardization module.

The standardization module 410 includes a user interface for adjusting the signal parameters of the stimulation signal. During a muscle identification session, the user can interact with the signal parameter user interface to configure stimulation signal parameters which elicit a strong pressure sensation during stimulation of sensitized muscle/fascia nociceptors. The configured stimulation signal parameters can be stored in a patient parameter table in the memory 132, or in an alternative format such as an electronic health record (e.g., electronic medical record (EMR)). An example signal parameter user interface 500 for controlling the carrier wave and modulation wave parameters is shown in FIG. 5. The example signal parameter user interface 500 includes rotary controls 502 and 504 to control the frequency parameters of the modulation wave and carrier wave, respectively. Two numerical displays 503 and 505 are shown beneath the rotary controls 502 and 504. The displayed numbers of 503 and 505 correspond to the frequency parameters selected using the rotary controls 502 and 504 respectively.

Altering the frequency parameters of the modulation wave or carrier wave using the corresponding rotary controls 502 or 504 adjusts the displayed numbers shown in numerical displays 503 and 505. Alternatively, the user can interact with one of the numerical displays 503 or 505 to adjust the frequency parameters of the modulation wave or carrier wave which alters the frequency of the corresponding rotary control 502 or 504. The frequency parameters the user inputs into the signal parameter user interface are stored in memory 132 (FIG. 3).

The signal parameter user interface 500 further includes amplitude displays 507 and 509. While the rotary controls 502 and 504 are used to control the frequency parameters of the stimulation signal, the amplitude displays 507 and 509 represent the amplitudes corresponding to the stimulation signal. For example, the left amplitude display 507 corresponds to the current amplitude being delivered to the stimulation head 110 and the right amplitude display 509 corresponds to the Fourier transform displaying the frequency power spectrum of the stimulation signal.

The signal parameter user interface 500 further includes an operational control 511 (e.g., stop button). The user can interact with the operational control 511 to initiate or terminate a muscle identification session after collecting one or more patient 10 responses. In some embodiments, the operational control 511 can be used to activate the stimulation signal in the stimulation head 110 to stimulate a sensitized muscle.

The signal parameter user interface 500 further includes a current amplitude display 513. Applying a voltage-based stimulation signal to the patient 10 includes applying a current to the patient 10 skin. The signal generator unit 124 generally controls the stimulation signal through voltage regulation to provide a constant current amplitude to the muscle and fascia being stimulated. The current amplitude is controlled to less than the contractile response threshold, e.g. approximately 0.4 A. In some embodiments, the current amplitude is controlled to 0.2 A. The current amplitude display 513 displays the instantaneous current amplitude being supplied by the signal generator unit 124 to the sensor head 110.

Figure 6:
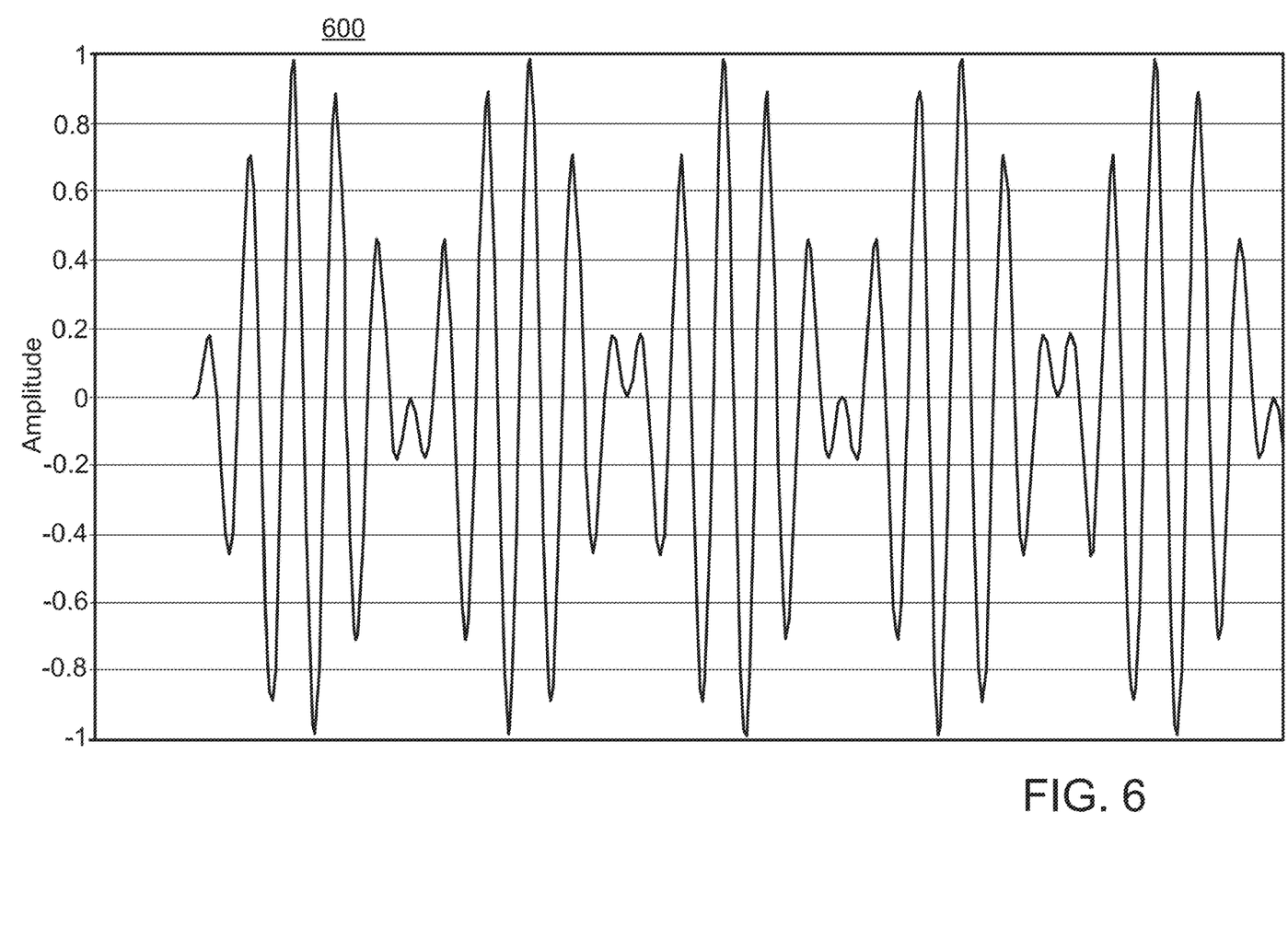
FIG. 6 is a graph depicting an example stimulation signal waveform.

FIG. 6 depicts a graph of an example stimulation signal waveform 600. FIG. 6 is a simulated normalized stimulation signal waveform 600 with a sinusoidal carrier wave at a frequency of 4.8 kHz multiplied by a sinusoidal modulation wave at a frequency of 0.48 kHz. The y-axis depicts the normalized amplitude of the waveform and the x-axis depicts approximately 0.006 seconds in time.

Figure 7:
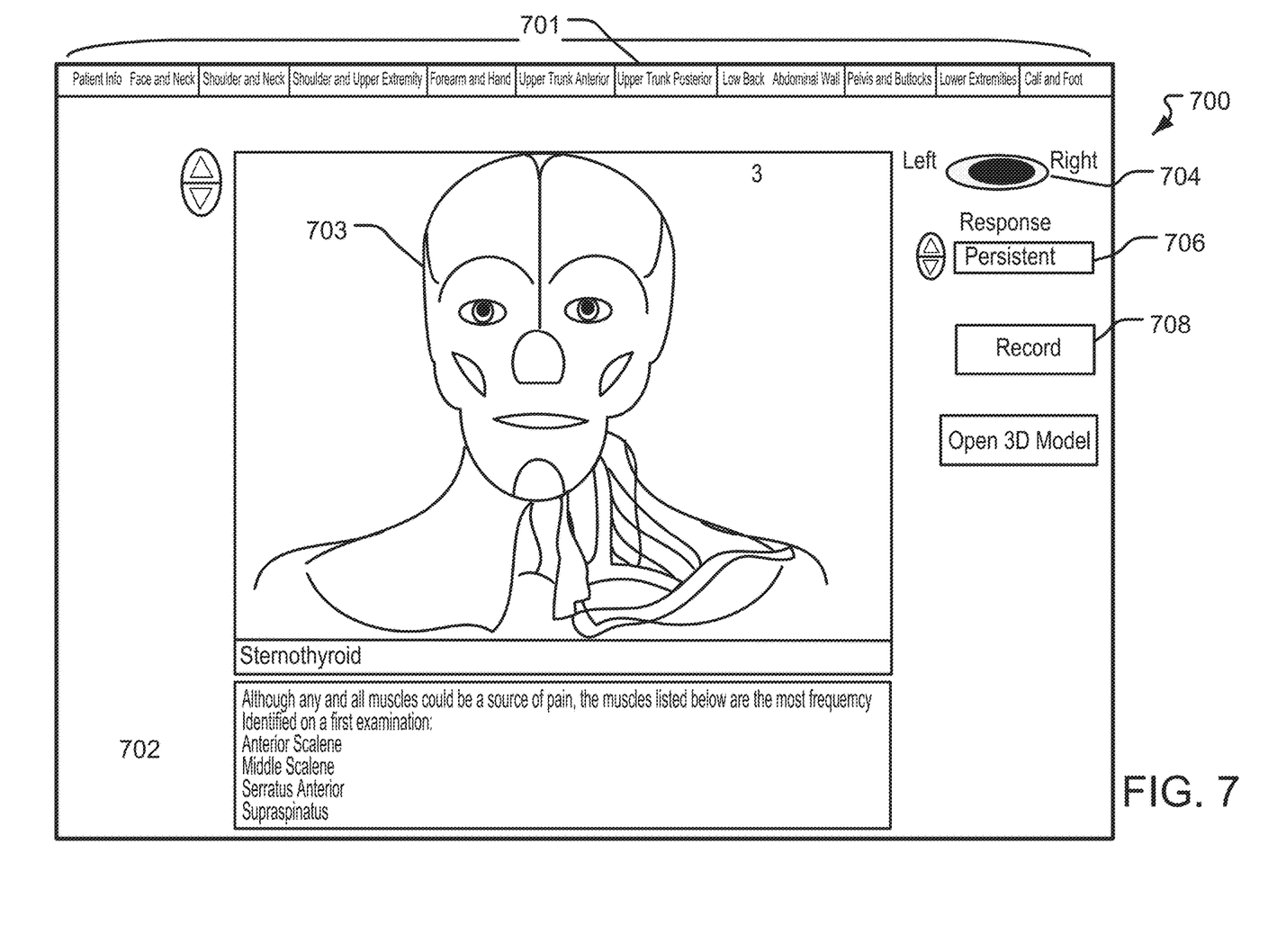
FIG. 7 is an image depicting an exemplary graphical user interface including a muscle group identification screen of the diagnosis module.

The user interface software 400 further includes a diagnosis module 412 for identifying sensitized muscle using interactive anatomical graphical depictions of muscle groups, individual muscles, and corresponding origin and insertion points. FIG. 7 depicts an example interactive graphical interface 700. Along the top of the interactive graphical interface 700 is a series of selectable tabs 701.

Each tab of the set of tabs 701 corresponds to a major muscle group and includes graphical depictions displaying the individual muscles of the group. As particular examples, the selectable tabs 701 can include major muscle groups such as face and neck muscles, shoulder and neck muscles, forearm and hand muscles, upper trunk anterior muscles, lower back muscles, abdominal wall muscles, and calf and foot muscles.

The interactive graphical interface 700 of FIG. 7 displays musculature depiction 703 of the bilateral anterior muscles of the face and shoulders, and the right anterior muscles of the neck, of a human subject. The user can interact with the musculature depiction 703 to select one or more muscles for potential sensitized nociceptor identification.

The user interacting with the musculature depiction 703 selects a displayed muscle for stimulation and the graphical interface 700 includes a text box 702 displaying information relevant to locating the selected muscle on the patient. The information can include, but is not limited to, origin and insertion point location, frequently identified muscles corresponding to pain described by the patient 10, muscle names, selected muscle identification landmarks, biological features nearby the selected muscles, nerves, vascular hazards, suggested stimulation signal parameters, or referred pain muscles associated with the selected muscle. In some embodiments, the information can be depicted graphically on the musculature depiction 703 additionally or alternatively to the information displayed in the text box 702.

The graphical interface 700 can include additional controls. For example, the graphical interface 700 includes a slider 704 for selecting right or left muscles on the graphical interface 700. The graphical interface 700 further includes a control 708 to transmit the patient 10 response to the processor 130 to store in the table or EMR stored in memory 132 (e.g., to record the response).

The user views the displayed information for the selected muscle and orients the stimulation probe 102 such that the stimulation head 110 is in contact with the surface of the patient skin proximal to the selected muscle. The signal generator 124 provides the stimulation signal to the stimulation head 110 and stimulates sensitized nociceptors in the selected muscle.

Figure 8:
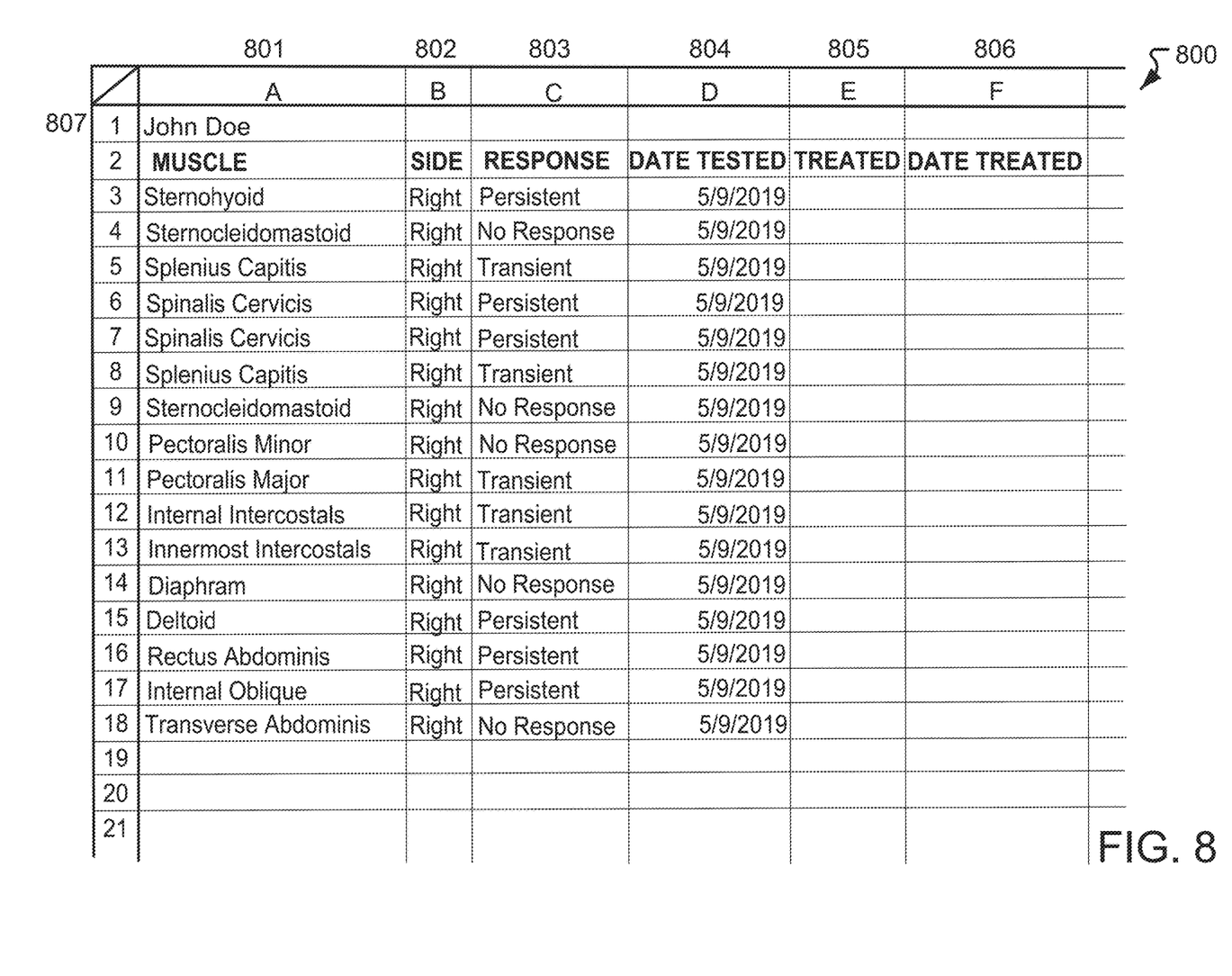
FIG. 8 is an image depicting an exemplary graphical user interface data entry screen of the treatment module.

The user interface software 400 further includes a treatment module 414 which catalogs and facilitates supplementary treatments of the identified muscles. As shown in FIG. 8, the treatment module 412 displays to the user a menu (e.g., a table) 800 including a selection of information regarding the identification and treatment status of muscles within a selected muscle group. The user views the information displayed by the treatment module 412 and determines one or more supplementary treatments from the displayed menu 800.

For example, the menu 800 can include a number of columns, each column containing a sequence of data (e.g., rows) corresponding to patient health information. For example, the menu 800 includes columns A through F (801 through 806). Column 801 displays the individual muscles of the abdominal muscle group, column 802 displays the patient side (e.g., right or left), column 803 displays the recorded patient response (e.g., no response, transient, or persistent pressure sensation), column 804 displays the most recent date the patient response corresponding to the muscle of the row was recorded, column 805 displays a Boolean variable (e.g., yes or no) indicating if the identified muscle received supplementary treatment, and column 806 displays the most recent date on which the supplementary treatment was delivered. The potential responses can include indicators of the level of pressure sensation experienced by the patient. As a non-limiting example, the patient 10 response may include "no pressure", "mild pressure", or "deep pressure." As a further example, the patient 10 response may include "no response," "transient," or "persistent."

In some embodiments, the data displayed in column 806 indicating the most recent date on which the supplementary treatment was delivered can include additional information regarding suggested supplementary treatment modes or suggested supplementary treatment schedules. For example, a number of muscles in a region may test out as sensitized. If the treatment chosen is an injection of sorts, a specific muscle is chosen for treatment.

As an example of additional information suggesting a supplementary treatment schedule, column 806 containing treatment dates can include color-coded information corresponding with a suggested treatment schedule. For example, a column 806 value displaying 'red' highlighting can indicate a treatment date within a three-month window. This information can facilitate a user not to treat that muscle that was treated in the past 3 months but rather to direct additional supplementary treatments to other identified sensitized muscles within the muscle group that have not yet been treated and are most likely the source of apparent ongoing or recurrent pain in a previously injected muscle.

In some embodiments, the menu 800 can include additional information to display to the user. For example, the menu 800 can display suggested treatment modes, deprecated treatment modes, patient diagnoses, or identifying patient information such as the patient name 807. Examples of supplementary treatment can include, but are not limited to, dry needling, trigger point injections, muscle tendon injections, injections of various medications, massage, electrical nerve stimulation, acupressure, acupuncture, photo-bio-modulation, or stretching.

The user interface software 400 further includes a reporting module 416 which displays and communicates collected and stored data from the EMR. The reporting module can receive from the user or from memory 132 information corresponding with the patient, identified muscles, medical history, date, time, or diagnoses and display them to the user in a report form, such as the report form 900 of FIG. 9.

Figure 9:
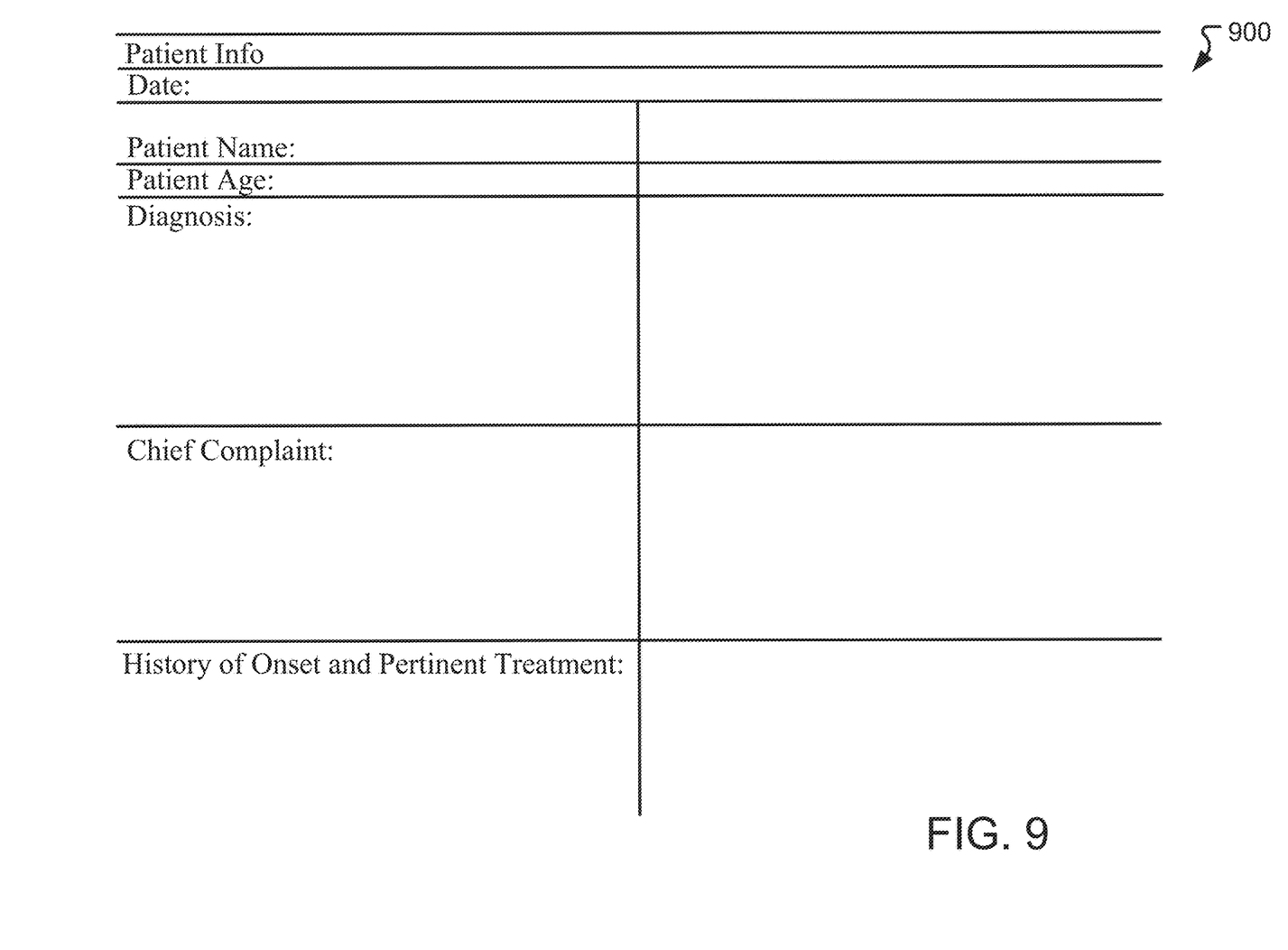
FIG. 9 is an image depicting an exemplary user interface patient response record of the recording module.

The exemplary report form 900 displays patient information fields including date, patient name, patient age, diagnosis, complaint, and historical treatment records. In some embodiments, the patient information fields can include patient identification values such as first name, last name, middle name, date of birth, patient weight, patient blood type, patient BMI, patient blood pressure, historical patient pain responses, patient complaint, patient complaint history, current diagnoses, historical diagnoses, present medication, or historical medication. The user can interact with the report form 900 to add, modify, or remove information to or from one or more fields. The reporting module 416 further includes one or more displayed controls for operation by the user. For example, the reporting module 416 can include a control for communicating the report form 900 to a local or networked computer, printer, laptop, mobile device, or server. In some implementations, the report form 900 can include additional patient information such as billing codes, insurance carrier, insurance group, insurance identification number, medical codes, or other patient billing values.

Figure 10:
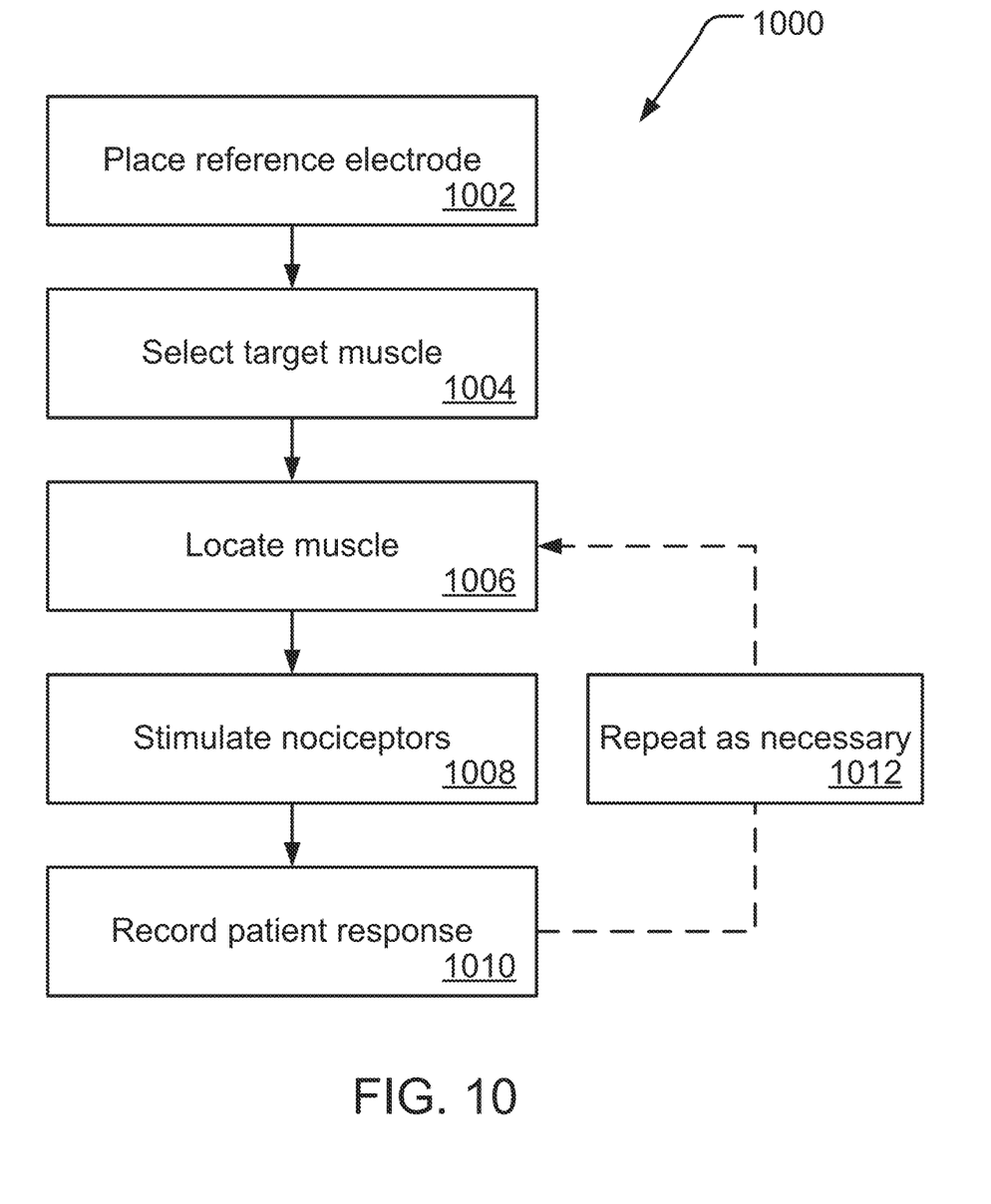
FIG. 10 is a flow chart detailing the method of sensitized nociceptor identification.

A method 1000 for identifying sensitized nociceptors using the nociceptor stimulation system 100 is shown in FIG. 10. In step 1002 of the method 1000, a reference electrode 103 is placed on an exposed portion of patient 10 skin to provide a ground for the stimulation signal. In some embodiments, the patient 10 skin impedance can be lowered with the use of a conductive material disposed between the reference electrode 103 and the patient 10 skin.

In step 1004, the user selects a target muscle for potential sensitized nociceptor identification using the display 122 of the control system 120. For example, in some embodiments the user interacts with the display 122, probe 102, or control buttons 106 or 108 to select from a list of muscles stored in the memory 132 of the device. The list of muscles can be a textual list of the muscles of the human body. In some embodiments, the list of muscles is presented to the user as a graphical depiction on the display 122. In some further embodiments, the list of muscles is presented to the user as an interactive graphical depiction on the display 122.

In step 1006 the user locates the selected muscle on the patient 10. Locating the muscle can include reading and/or viewing information displayed on the graphical interface 600 and/or in the text box 602 to establish physiological landmarks signifying the location of the muscle on the patient 10. Locating the muscle can include palpation of a region identified by the graphical interface 600.

In step 1008 of the method 1000, the user stimulates the nociceptors of the selected muscle using the nociceptor stimulation system 100. The conductive sensor head 110 of the probe 102 is placed against the patient 10 skin in proximity to the selected muscle. In some embodiments, the patient 10 skin impedance can be lowered with the use of a conductive material disposed between the sensor head 110 and the patient 10 skin.

The stimulation signal parameters, including carrier wave frequency and amplitude, and modulation wave frequency and amplitude, are received by the signal generator 124 in the control system 120, and a stimulation signal is generated by combining (e.g., mixing) the carrier signal and the modulation signal together.

The stimulation signal is transmitted to the communications unit 126 from which the probe 102 receives the stimulation signal. The user operates the modulation button 104 which transmits the stimulation signal to the sensor head 110. The conductive contact between the sensor head 110, any intermediary conductive material, and the patient 10 skin transmits the stimulation signal to the muscle beneath the sensor head 110.

The sensitized nociceptors present within the tissue and enshrouding fascia of the selected muscle, if any, receive the stimulation signal. The stimulation signal stimulates the sensitized nociceptors above the respective activation threshold thereby producing an activation potential and transmitting a response through the patient's nervous system. The activation potential of sensitized nociceptors produces a pressure sensation in the muscle experienced by the patient 10. The patient 10 can experience the induced pressure sensation along a spectrum of sensation magnitudes.

The user prompts the patient 10 to report their experienced pressure sensation according to a limited list of responses, such as the list of responses noted above. The patient 10 responds by electing a response from the list of responses which corresponds to the experienced pressure sensation.

In step 1010, the user records the patient 10 response. The user can record the patient 10 response by operating the control buttons 106 or 108, by commanding the control system 120 to record the response, or by interacting with the control system 120 directly, for example, through the display 122.

The muscle identification process of muscle location (step 1006), nociceptor stimulation (step 1008), and patient 10 response recording (step 1010) can be repeated (step 1012) for several muscles.

Figure 11:
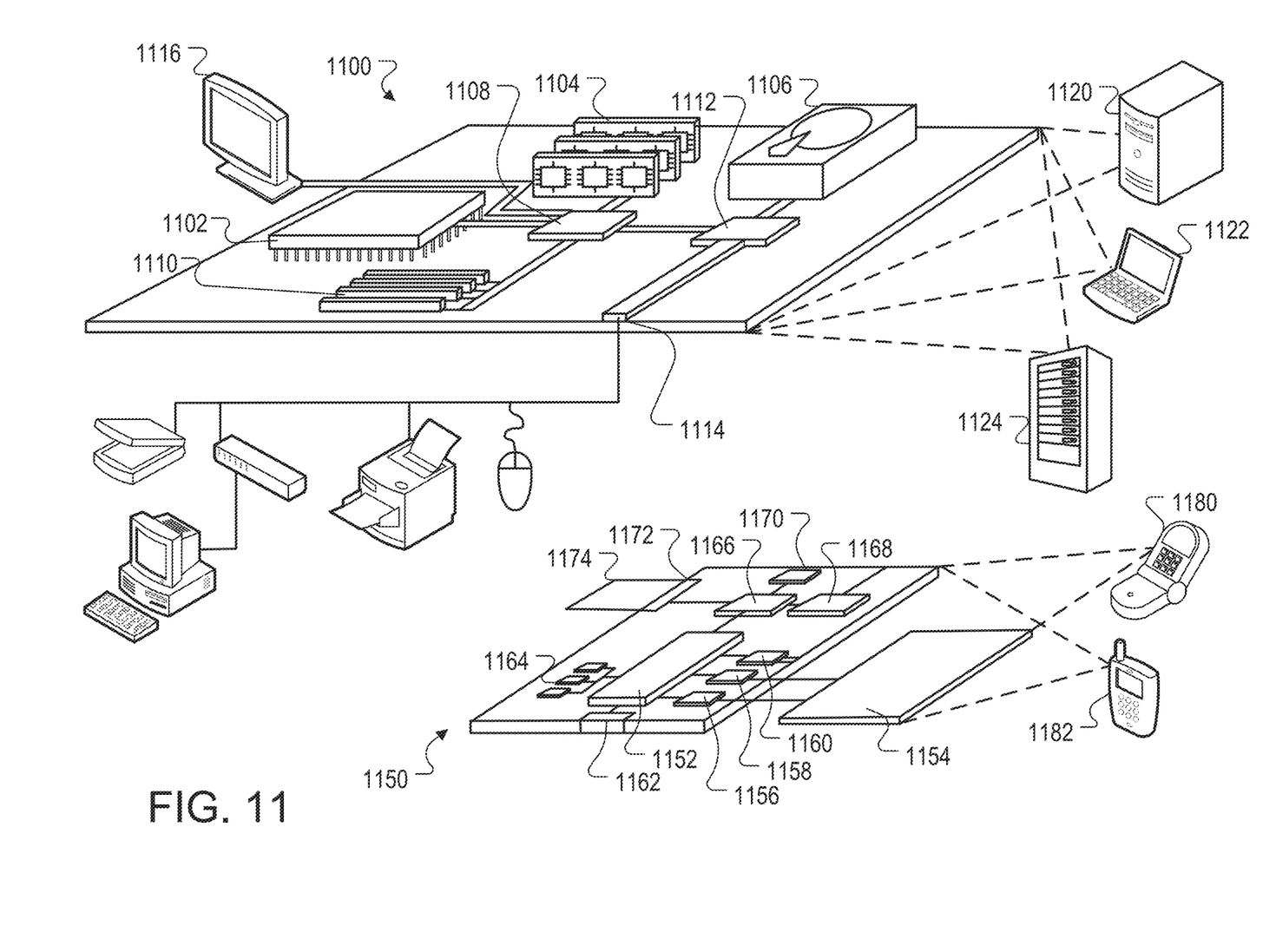
FIG. 11 is a schematic diagram of an example computer system and components.

As noted previously, the systems and methods disclosed above utilize data processing apparatus to implement aspects of the sensitized muscle identification system described. FIG. 11 shows an example of a computing device 1100 and a mobile computing device 1150 that can be used as data processing apparatuses to implement the techniques described here. The computing device 1100 is intended to represent various forms of digital computers, such as laptops, desktops, workstations, personal digital assistants, servers, blade servers, mainframes, and other appropriate computers. The mobile computing device 1150 is intended to represent various forms of mobile devices, such as personal digital assistants, cellular telephones, smartphones, and other similar computing devices. The components shown here, their connections and relationships, and their functions, are meant to be examples only, and are not meant to be limiting.

The computing device 1100 includes a processor 1102, a memory 1104, a storage device 1106, a high-speed interface 1108 connecting to the memory 1104 and multiple high-speed expansion ports 1110, and a low-speed interface 1112 connecting to a low-speed expansion port 1114 and the storage device 1106. Each of the processor 1102, the memory 1104, the storage device 1106, the high-speed interface 1108, the high-speed expansion ports 1110, and the low-speed interface 1112, are interconnected using various busses, and may be mounted on a common motherboard or in other manners as appropriate. The processor 1102 can process instructions for execution within the computing device 1100, including instructions stored in the memory 1104 or on the storage device 1106 to display graphical information for a GUI on an external input/output device, such as a display 1116 coupled to the high-speed interface 1108. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 1104 stores information within the computing device 1100. In some implementations, the memory 1104 is a volatile memory unit or units. In some implementations, the memory 1104 is a non-volatile memory unit or units. The memory 1104 may also be another form of computer-readable medium, such as a magnetic or optical disk.

The storage device 1106 is capable of providing mass storage for the computing device 1100. In some implementations, the storage device 1106 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 1102), perform one or more methods, such as those described above. The instructions can also be stored by one or more storage devices such as computer- or machine-readable mediums (for example, the memory 1104, the storage device 1106, or memory on the processor 1102).

The high-speed interface 1108 manages bandwidth-intensive operations for the computing device 1100, while the low-speed interface 1112 manages lower bandwidth-intensive operations. Such allocation of functions is an example only. In some implementations, the high-speed interface 1108 is coupled to the memory 1104, the display 1116 (e.g., through a graphics processor or accelerator), and to the high-speed expansion ports 1110, which may accept various expansion cards (not shown). In the implementation, the low-speed interface 1112 is coupled to the storage device 1106 and the low-speed expansion port 1114. The low-speed expansion port 1114, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 1100 may be implemented in a number of different forms, as shown in the figure. For example, it may be implemented as a standard server 1120, or multiple times in a group of such servers. In addition, it may be implemented in a personal computer such as a laptop computer 1122. It may also be implemented as part of a rack server system 1124. Alternatively, components from the computing device 1100 may be combined with other components in a mobile device (not shown), such as a mobile computing device 1150. Each of such devices may contain one or more of the computing device 1100 and the mobile computing device 1150, and an entire system may be made up of multiple computing devices communicating with each other.

The mobile computing device 1150 includes a processor 1152, a memory 1164, an input/output device such as a display 1154, a communication interface 1166, and a transceiver 1168, among other components. The mobile computing device 1150 may also be provided with a storage device, such as a micro-drive or other device, to provide additional storage. Each of the processor 1152, the memory 1164, the display 1154, the communication interface 1166, and the transceiver 1168, are interconnected using various buses, and several of the components may be mounted on a common motherboard or in other manners as appropriate.

The processor 1152 can execute instructions within the mobile computing device 1150, including instructions stored in the memory 1164. The processor 1152 may be implemented as a chipset of chips that include separate and multiple analog and digital processors. The processor 1152 may provide, for example, for coordination of the other components of the mobile computing device 1150, such as control of user interfaces, applications run by the mobile computing device 1150, and wireless communication by the mobile computing device 1150.

The processor 1152 may communicate with a user through a control interface 1158 and a display interface 1156 coupled to the display 1154. The display 1154 may be, for example, a TFT (Thin-Film-Transistor Liquid Crystal Display) display or an OLED (Organic Light Emitting Diode) display, or other appropriate display technology. The display interface 1156 may comprise appropriate circuitry for driving the display 1154 to present graphical and other information to a user. The control interface 1158 may receive commands from a user and convert them for submission to the processor 1152. In addition, an external interface 1162 may provide communication with the processor 1152, so as to enable near area communication of the mobile computing device 1150 with other devices. The external interface 1162 may provide, for example, for wired communication in some implementations, or for wireless communication in other implementations, and multiple interfaces may also be used.

The memory 1164 stores information within the mobile computing device 1150. The memory 1164 can be implemented as one or more of a computer-readable medium or media, a volatile memory unit or units, or a non-volatile memory unit or units. An expansion memory 1174 may also be provided and connected to the mobile computing device 1150 through an expansion interface 1172, which may include, for example, a SIMM (Single In Line Memory Module) card interface. The expansion memory 1174 may provide extra storage space for the mobile computing device 1150, or may also store applications or other information for the mobile computing device 1150. Specifically, the expansion memory 1174 may include instructions to carry out or supplement the processes described above, and may include secure information also. Thus, for example, the expansion memory 1174 may be provide as a security module for the mobile computing device 1150, and may be programmed with instructions that permit secure use of the mobile computing device 1150. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. The instructions, when executed by one or more processing devices (for example, processor 1152), perform one or more methods, such as those described above. The instructions can also be stored by one or more storage devices, such as one or more computer- or machine-readable mediums (for example, the memory 1164, the expansion memory 1174, or memory on the processor 1152). In some implementations, the instructions can be received in a propagated signal, for example, over the transceiver 768 or the external interface 1162.

The mobile computing device 1150 may communicate wirelessly through the communication interface 1166, which may include digital signal processing circuitry where necessary. The communication interface 1166 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1168 using a radio-frequency. In addition, short-range communication may occur, such as using a Bluetooth, Wi-Fi, or other such transceiver (not shown). In addition, a GPS (Global Positioning System) receiver module 1170 may provide additional navigation- and location-related wireless data to the mobile computing device 1150, which may be used as appropriate by applications running on the mobile computing device 1150.

The mobile computing device 1150 may also communicate audibly using an audio codec 1160, which may receive spoken information from a user and convert it to usable digital information. The audio codec 1160 may likewise generate audible sound for a user, such as through a speaker, e.g., in a handset of the mobile computing device 1150. Such sound may include sound from voice telephone calls, may include recorded sound (e.g., voice messages, music files, etc.) and may also include sound generated by applications operating on the mobile computing device 1150.

The mobile computing device 1150 may be implemented in a number of different forms, as shown in the figure. For example, it may be implemented as a cellular telephone 1180. It may also be implemented as part of a smart-phone 1182, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., an OLED (organic light emitting diode) display or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some embodiments, the computing system can be cloud based and/or centrally processing data. In such case anonymous input and output data can be stored for further analysis. In a cloud based and/or processing center set-up, compared to distributed processing, it can be easier to ensure data quality, and accomplish maintenance and updates to the calculation engine, compliance to data privacy regulations and/or troubleshooting.

Although various illustrative examples have been described in detail above, any of several changes may be made to various embodiments without departing from the scope of the disclosure as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the apparatuses and methods as it is set forth in the claims.

Terminology used herein is for the purpose of describing particular embodiments only and is not intended to be limiting. For example, as used herein, the singular forms "a", "an" and "the" are intended to include the plural forms as well, unless the context clearly indicates otherwise. As used herein, the term "and/or" includes any and all combinations of one or more of the associated listed items. When a feature or element is referred to as being "mounted", "connected", "attached" or "coupled" to another feature or element, it can be directly mounted, connected, attached or coupled to the other feature or element or intervening features or elements may be present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present apparatuses and methods.

Various embodiments may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

Although various examples have been described in detail above, other modifications are possible. Accordingly, other implementations are within the scope of the following claims.

What is claimed is:

1. A sensitized muscle identification method comprising:
   inputting an identifier of a muscle group into a sensitized muscle identification system;
   receiving, from the sensitized muscle identification system, a compilation of muscles within the muscle group;
   receiving from a patient a muscle group producing a pain sensation;
   inputting the muscle group into the sensitized muscle identification system;
   receiving from the sensitized muscle identification system a table of muscles within the muscle group;
   selecting a first muscle to be tested from within the muscle group;
   placing a sensor head of an electrical stimulation probe of the sensitized muscle identification system in contact with a first skin surface of the patient, the first skin surface being proximate to the first muscle; and
   applying a stimulation signal to the first skin surface using the sensor head to induce an activation potential in a plurality of sensitized nociceptors present in the first muscle while remaining below a threshold that induces a contractile response in the first muscle,
   wherein the activation potential in the plurality of sensitized nociceptors induces a sensation of discomfort in the first muscle that is experienced by the patient.

2. The sensitized muscle identification method of claim 1, the method further comprising recording a patient response corresponding to the sensation of discomfort experienced by the patient.

3. The sensitized muscle identification method of claim 1, further comprising determining a treatment method for the first muscle based upon the sensation of discomfort in the first muscle that is experienced by the patient.

4. The sensitized muscle identification method of claim 1, the method further comprising:
   selecting a second muscle to be tested from within the muscle group;
   placing the sensor head of the electrical stimulation probe in contact with a second skin surface of the patient, the second skin surface being proximate to the second muscle; and
   applying a stimulation signal to the second skin surface using the sensor head to induce an activation potential in a plurality of sensitized nociceptors present in the second muscle while remaining below a threshold that induces a contractile response in the second muscle,
   wherein the activation potential in the plurality of sensitized nociceptors induces a sensation of discomfort in the second muscle that is experienced by the patient.

5. The sensitized muscle identification method of claim 1, the method further comprising, between selecting the first muscle and placing the stimulation head, applying a conductive material to the first skin surface proximate to the first muscle.

6. The sensitized muscle identification method of claim 5, wherein the conductive material is a gel, liquid, paste, or powder.

7. The sensitized muscle identification method of claim 2, wherein the recorded patient response is electronically communicated to a clinician user.

8. The sensitized muscle identification method of claim 3, wherein the treatment method comprises dry needling, trigger point injections, muscle tendon injections, injections of various medications, massage, electrical nerve stimulation, acupressure, acupuncture, photo-bio-modulation, exercises, and/or stretching.

9. The sensitized muscle identification method of claim 1, further comprising, after selecting the first muscle, receiving a location of the plurality of sensitized nociceptors within the first muscle from the sensitized muscle identification system, and the first skin surface is proximate to the location of the plurality of sensitized nociceptors.

* * * * *